United States Patent
Dubuffet et al.

(10) Patent No.: US 7,279,583 B2
(45) Date of Patent: Oct. 9, 2007

(54) PROCESS FOR THE SYNTHESIS OF PERINDOPRIL AND PHARMACEUTICALLY ACCEPTABLE SALTS THEREOF

(75) Inventors: Thierry Dubuffet, Autretot (FR); Jean-Pierre Lecouve, Le Havre (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/582,283

(22) PCT Filed: Dec. 9, 2004

(86) PCT No.: PCT/FR2004/003166

§ 371 (c)(1), (2), (4) Date: Jun. 9, 2006

(87) PCT Pub. No.: WO2005/066198

PCT Pub. Date: Jul. 21, 2005

(65) Prior Publication Data

US 2007/0093663 A1    Apr. 26, 2007

(30) Foreign Application Priority Data

Dec. 10, 2003    (EP) .................................. 03293084

(51) Int. Cl.
*C07D 209/12*    (2006.01)
(52) U.S. Cl. .................................... 548/452
(58) Field of Classification Search ................. 548/452
See application file for complete search history.

(56) References Cited

FOREIGN PATENT DOCUMENTS

WO    01/58868    8/2001

OTHER PUBLICATIONS

Li, Peng, et al., "New and highly efficient immonium-type peptide coupling reagents: syntheisi, mechanism, and application" TETRAHEDRON, vol. 56, No. 26, p. 4437-4445, 2000.

Li, Peng, et al., "BOMI—a novel peptide coupling reagent" Tetrahedron Letters, vol. 40, No. 18, p. 3605-3608, 1999.

Li, Peng, et al., "The development of highly efficient anium-type peptide coupling reagents based upon rational molecular design" Journal of Peptide Research, vol. 58, No. 2, p. 129-139, 2001.

Coste, Jacques, et al. "Oxybenzotriazole free peptide coupling reagents for N-methylate amino acids" Tetrahedron Letters, vol. 32, No. 17, p. 1967-1970, 1991.

Carpino, Louis, et al., "Effect of Tertiary basis on )-benzotriazolyluronium salt-induced peptide segment coupling" Journal of Organic Chemistry, vol. 59, No. 4, p. 695-698, 1994.

Chen, Shaoqing, et al, "A coupling reagent for peptide synthesis. Benzotriazolyloxybis(pyrrolidine)carbonium hexafluorophosphate(BBC)" Tetrahedron Letters, vol. 33, No. 5, p. 647-650, 1992.

International Search Report for PCT/FR2004/003166—May 3, 2005.
European Search Report for EP 03293084—Mar. 18, 2004.

*Primary Examiner*—Kamal A. Saeed
*Assistant Examiner*—Michael P. Barker
(74) *Attorney, Agent, or Firm*—Hueschen and Sage

(57) ABSTRACT

Process for the industrial synthesis of perindopril of formula (I):

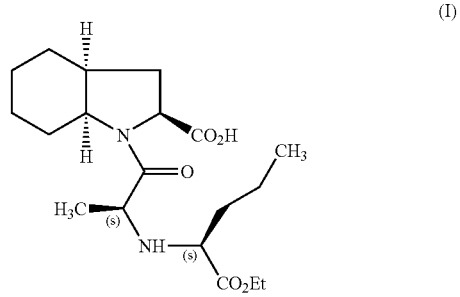

and pharmaceutically acceptable salts thereof.

6 Claims, No Drawings

PROCESS FOR THE SYNTHESIS OF PERINDOPRIL AND PHARMACEUTICALLY ACCEPTABLE SALTS THEREOF

The present invention relates to a process for the synthesis of perindopril of formula (I):

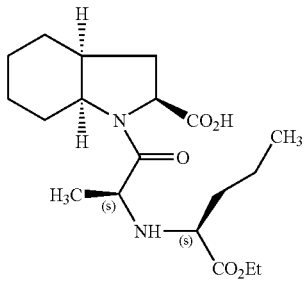

(I)

and pharmaceutically acceptable salts thereof.

Perindopril and its pharmaceutically acceptable salts, and more especially its tert-butylamine salt, have valuable pharmacological properties.

Their principal property is that of inhibiting angiotensin I converting enzyme (or kininase II), which allows, on the one hand, prevention of the conversion of the decapeptide angiotensin I to the octapeptide angiotensin II (a vasoconstrictor) and, on the other hand, prevention of the degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in European patent specification EP 0 049 658.

In view of the pharmaceutical value of this compound, it has been important to be able to obtain it by an effective synthesis process, readily transposable to an industrial scale, that leads to perindopril in a good yield and, especially, with excellent purity.

Patent specification EP 0 308 341 describes the industrial synthesis of perindopril by the coupling of (2S,3aS,7aS)-octahydroindole-2-carboxylic acid benzyl ester with N-[(S)-1-carboxybutyl]-(S)-alanine ethyl ester in the presence of dicyclohexylcarbodiimide, followed by deprotection of the carboxylic group of the heterocycle by catalytic hydrogenation.

That process has disadvantages related to use of the dicyclohexylcarbodiimide.

The Applicant has developed a process for the synthesis of perindopril that uses other coupling agents.

More specifically, the present invention relates to a process for the synthesis of perindopril, which process is characterised in that the benzyl ester of formula (IIa) or (IIb):

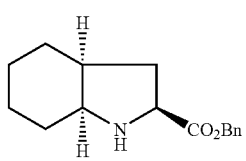

(IIa)

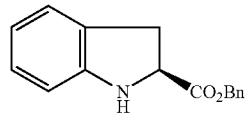

(IIb)

or an addition salt of the ester of formula (IIa) or (IIb) with a mineral acid or organic acid is reacted with the compound of formula (III):

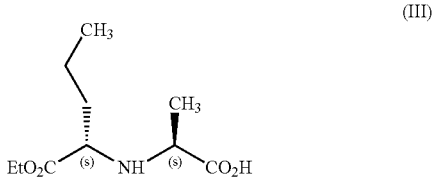

(III)

in the presence of a coupling agent selected from the following reagents and pairs of reagents:
(1,3-dimethylaminopropyl)-3-ethyl-carbodiimide hydrochloride,
(1,3-dimethylaminopropyl)-3-ethyl-carbodiimide hydrochloride/1-hydroxybenzotriazole,
(1,3-dimethylaminopropyl)-3-ethyl-carbodiimide hydrochloride/1-hydroxy-7-azabenzo-triazole,
(1,3-dimethylaminopropyl)-3-ethyl-carbodiimide hydrochloride/N-hydroxysuccinimide,
(1,3-dimethylaminopropyl)-3-ethyl-carbodiimide hydrochloride/3-hydroxy-3,4-dihydro-4-oxo-1,2,3-benzotriazine,
(1,3-dimethylaminopropyl)-3-ethyl-carbodiimide hydrochloride/N-hydroxyphthalimide,
dicyclohexylcarbodiimide/1-hydroxy-7-azabenzotriazole,
dicyclohexylcarbodiimide/N-hydroxysuccinimide,
dicyclohexylcarbodiimide/3-hydroxy-3,4-dihydro-4-oxo-1,2,3-benzotriazine,
dicyclohexylcarbodiimide/N-hydroxyphthalimide,
O-(benzotriazol-1-yl)-1,1,3,3-tetramethyluronium hexafluorophosphate,
O-(7-azabenzotriazol-1-yl)-1,1,3,3-tetramethyluronium hexafluorophosphate,
O-(benzotriazol-1-yl)-1,1,3,3-tetramethyluronium tetrafluoroborate,
benzotriazol-1-yl-oxytripyrrolidinophosphonium hexafluorophosphate,
benzotriazol-1-yl-oxy-tris(dimethylamino)phosphonium hexafluorophosphate,
O-(benzotriazol-1-yl)-1,1,3,3-bis(tetramethylene)uronium hexafluorophosphate,
O-(benzotriazol-1-yl)-1,1,3,3-bis(pentamethylene)uronium hexafluorophosphate,
chloro-tripyrrolidinophosphonium hexafluorophosphate,
chloro-1,1,3,3-bis(tetramethylene)formamidinium hexafluorophosphate,
chloro-1,1,3,3-bis(pentamethylene)formamidinium hexafluorophosphate,
N-ethoxycarbonyl-2-ethoxy-1,2-dihydroquinoline,
O-[(ethoxycarbonyl)-cyanomethyleneamino]-1,1,3,3-tetramethyluronium tetrafluoroborate, O-(3,4-dihydro-4-oxo-1,2,3-benzotriazin-3-yl)-1,1,3,3-tetramethyluronium tetrafluoroborate, O-(3,4-dihydro-4-oxo-1,2,3-benzotriazin-3-yl)-1,1,3,3-tetramethyluronium tetrafluoroborate/1-hydroxybenzotriazole, O-(3,4-dihydro-4-oxo-1,2,3-benzotriazin-3-yl)-1,1,3,3-tetramethyluronium tetrafluoroborate/N-methylmorpholine, O-(3,4-dihydro-4-oxo-1,2,3-benzotriazin-3-yl)-1,1,3,3-tetramethyluronium tetrafluoroborate/collidine, O-(1,2-dihydro-2-oxo-1-pyridyl)-1,1,3,3-tetramethyluronium tetrafluoroborate, O-(1,2-dihydro-2-oxo-1-pyridyl)-1,1,3,3-tetramethyluronium tetrafluoroborate/1-hydroxybenzotriazole, O-(1,2-dihydro-2-oxo-1-pyridyl)-1,1,3,3-bis(tetramethylene)uronium hexafluorophosphate, O-(1,2-dihydro-2-oxo-1-pyridyl)-1,1,3,3-bis(tetramethylene)uronium hexafluoro-phosphate/1-hydroxy-benzotriazole, O-(N-succinimidyl)-1,1,3,3-tetramethyluronium tetrafluoroborate, O-(N-succinimidyl)-1,1,3,3-bis(tetramethylene)uronium tetrafluoroborate, O-(N-succinimidyl)-1,1,3,3-bis(tetramethylene)uronium tetrafluoroborate/1-hydroxy-benzotriazole, O-(5-norbornene-2,3-dicarboximido)-1,1,3,3-tetramethyluronium tetrafluoroborate, propanephosphonic anhydride, N-hydroxy-5-norbornene-2,3-dicarboxylic acid imide, and N-hydroxy-1,2-dihydro-2-oxo-pyridine, optionally in the presence of a base, to yield, after catalytic hydrogenation in the presence of palladium, perindopril of formula (I), which is converted, if desired, into a pharmaceutically acceptable salt such as the tert-butylamine salt.

When the compound of formula (IIa) is used as starting material, the catalytic hydrogenation is preferably carried out under a hydrogen pressure of less than 10 bars.

When the compound of formula (IIb) is used as starting material, the catalytic hydrogenation is preferably carried out under a hydrogen pressure of from 10 to 35 bars.

The example hereinbelow illustrates the invention.

EXAMPLE 1

Benzyl (2S,3aS,7aS)-1-{((2S)-2-[(1S)-1-(ethoxycarbonyl)-butylamino]-propionyl}-octahydro-1H-indole-2-carboxylate 200 g of (2S,3aS,7aS)-octahydroindole-2-carboxylic acid benzyl ester para-toluene-sulphonate, 65 ml of triethylamine and 1 litre of ethyl acetate are introduced into a stirred reactor, followed, after stirring for 10 minutes at ambient temperature, by 100 g of N-[(S)-ethoxycarbonyl-1-butyl]-(S)-alanine and 175 g of O-(benzotriazol-1-yl)-1,1,3,3-bis(tetra-methylene)uronium hexafluorophosphate. The heterogeneous mixture is then heated at 30° C. for 3 hours whilst stirring well and is then cooled to 0° C. and filtered.

The filtrate is then washed and subsequently evaporated to dryness to yield the expected product.

EXAMPLE 2

(2S,3aS,7aS)-1-{(2S)-2-[(1S)-1-(Ethoxycarbonyl)-butylamino]-propionyl}-octahydro-1H-indole-2-carboxylic acid The residue obtained in the previous step (200 g) is dissolved in 200 ml of methyl-cyclohexane and transferred to a hydrogenator; 26 g of 5% palladium-on-carbon suspended in 80 ml of methylcyclohexane are then added, followed by 640 ml of water.

The mixture is then hydrogenated under a pressure of 0.5 bar at a temperature of from 15 to 30° C., until the theoretical amount of hydrogen has been absorbed.

After filtering off the catalyst, the aqueous phase of the filtrate is washed with methylcyclohexane and then lyophilised to yield the expected product in a yield of 94%.

EXAMPLE 3

(2S,3aS,7aS)-1-{(2S)-2-[(1S)-(Ethoxycarbonyl)-butylamino]-propionyl}-octahydro-1H-indole-2-carboxylic acid tert-butylamine salt The lyophilisate obtained in the previous step (200 g) is dissolved in 2.8 litres of ethyl acetate, and then 44 g of tert-butylamine and 400 ml of ethyl acetate are added.

The suspension obtained is then refluxed until dissolution is complete; then the solution obtained is filtered whilst hot and cooled to a temperature of 15-20° C., with stirring.

The precipitate obtained is then filtered off, made into a paste again using ethyl acetate, dried and then ground to yield the expected product in a yield of 95%.

What is claimed is:

1. A process for the industrial synthesis of perindopril of formula (I)

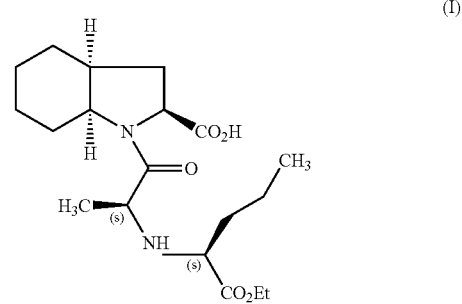

(I)

and pharmaceutically acceptable salts thereof, wherein a benzyl ester of formula (IIa) or (IIb):

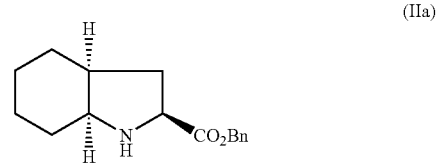

(IIa)

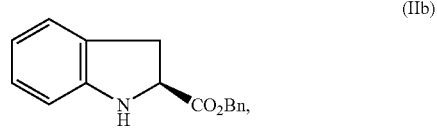

(IIb)

or an addition salt of the ester of formula (IIa) or (IIb) with a mineral acid or organic acid, is reacted with a compound of formula (III):

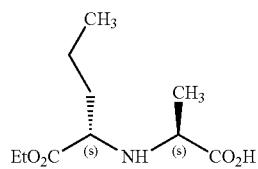

in the presence of a coupling agent selected from:
1-(3-dimethylaminopropyl)-3-ethyl-carbodiimide hydrochloride/1-hydroxybenzotriazole and propanephosphonic anhydride, optionally in the presence of a base,
to yield, after catalytic hydrogenation in the presence of palladium, perindopril of formula (I), which is converted, if desired, into a pharmaceutically acceptable salt.

2. The process of claim 1 for the synthesis of perindopril in the form of its tert-butylamine salt.

3. The process of claim 1, wherein the compound of formula (IIa) is used as starting material.

4. The process of claim 1, wherein the compound of formula (IIb) is used as starting material.

5. The process of claim 3, wherein the hydrogenation reaction is carried out under a hydrogen pressure of less than 10 bars.

6. The process of claim 4, wherein the hydrogenation reaction is carried out under a hydrogen pressure of from 10 to 35 bars.

* * * * *